United States Patent [19]

Warren

[11] 4,433,075
[45] Feb. 21, 1984

[54] QUALITY CONTROL PROCEDURE FOR DETERMINING PARTICLE CONCENTRATION IN POLYMERS

[75] Inventor: Paul C. Warren, Far Hills, N.J.

[73] Assignee: Bell Telephone Laboratories, Incorporated, Murray Hill, N.J.

[21] Appl. No.: 441,222

[22] Filed: Nov. 12, 1982

[51] Int. Cl.$^3$ .......................... C08J 3/00; C08K 3/04
[52] U.S. Cl. .................................... 523/303; 524/113; 524/567
[58] Field of Search ................. 523/303; 524/567, 113

[56] References Cited

PUBLICATIONS

Cobler et al., "The Science & Technology of Polymer Films", vol. I, pp. 780–785, Interscience Publishers Sweeting Ed. 1968.
Chem. Abs. 87-185150m, (1977), Dadivanyan et al.
Chem. Abs. 75-135244b, (1971), Olson.

*Primary Examiner*—Melvyn I. Marquis
*Assistant Examiner*—Herbert J. Lilling
*Attorney, Agent, or Firm*—Bruce S. Schneider

[57] ABSTRACT

An expeditious method has been found for measuring the concentration of particles found in a polymer composition such as in wire and cable jackets. This procedure involves dissolving the polymer composition in a suitable solvent so that the particles form a dispersion in the solvent. The concentration of these particles in the solvent is then measured through transmission spectroscopy and this value is related to the concentration of the particles present in the original polymer body.

9 Claims, 1 Drawing Figure

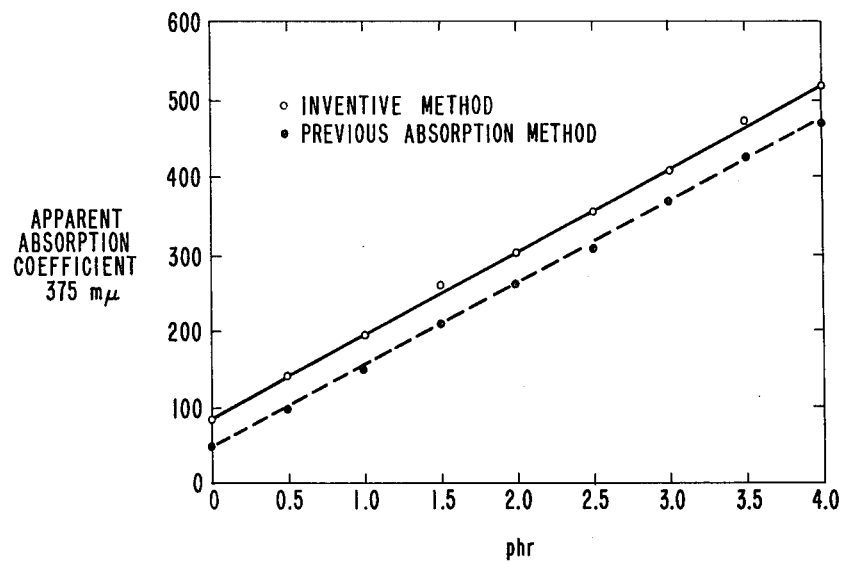

QUALITY CONTROL PROCEDURE FOR DETERMINING PARTICLE CONCENTRATION IN POLYMERS

BACKGROUND OF THE INVENTION

1. Field of the Invention

This invention relates to measurement techniques and, in particular, to measurement techniques involving polymer bodies.

2. Art Background

The use of particulate matter blended with polymers such as polyvinyl chloride (PVC) is quite common. Many widely used commercial products such as wire coatings and wire jacketings rely on such blends to produce properties necessary for their appropriate functioning. For example, it has been found that polymers such as PVC degrade when exposed to ultraviolet light. Various additives, e.g., carbon black, have been incorporated into PVC to avoid degradation during applications such as outdoor wiring where ultraviolet exposure is relatively high.

Additionally, particulate additives other than carbon black are employed to modify the properties of polymers. For example, particulate titanium oxide is often added to polymers such as polyethylene and PVC. A uniform distribution of these particulate additives at an appropriate concentration level in the polymer body significantly influences additive efficacy. (If the concentration is not uniform, typically the additive is less efficacious.) Thus, a quality control procedure historically has been considered necessary to ensure that appropriate particulate additive levels are employed. Initially in the case of carbon black, a simple microscopic examination was utilized. In this technique, a sample was viewed under an optical microscope and subjectively compared to a sample which had the desired properties. If the comparison was satisfactory, the sample was also considered satisfactory. Obviously, this method is very qualitative and often lead to the use of material which ultimately proved to be unsatisfactory.

In an attempt to quantify concentration measurements a spectroscopic technique was then developed. This procedure (which was eventually standardized as ASTM D3349, described in the 1981 Annual Book of The ASTM Book of Standards, American Society for Testing Materials, Part 36, 829–834) involved the preparation of a very thin sample whose absorption is measured. The quantity of light absorbed by the sample is correlated with a concentration of the carbon black in the initial sample.

Although the absorption test is significantly more quantitative than optical microscopy, it is also substantially more complicated and time consuming. The absorption test requires the preparation of a very thin compression molded film which must be completely pinhole free. (Films thicker than approximately 0.0005 inch substantially attenuate incident light. To overcome this problem, expedients must be employed which significantly reduce the accuracy of the procedure.) However, the preparation of such a thin film requires extraordinary skill. Even once the sample is prepared, its transfer to the absorption spectrophotometer is quite difficult. The film tends, through electrostatic interactions, to cling to the material upon which it is prepared. Thus, transfer often results in either torn, useless films or films which have been stretched to produce nonuniformities. Due to induced nonuniformity and the use of undesirably thick films, substantial disagreement between measurements made at different facilities on the same sample is often produced.

The absorption technique is more quantitative than the initial microscopic procedure, but it is not entirely consistent and the improvement over microscopy is balanced by a significant increase in complexity and preparation time. However, both increased complexity and time consumption are undesirable for applications such as those involved in quality control.

SUMMARY OF THE INVENTION

An expeditious, reliable procedure for measuring the concentration of particles blended in a polymer body has been found. This procedure involves the solvation of the polymer body in a suitable solvent. For example, PVC is soluble in a number of solvents such as tetrahydrofuran (THF). Generally, the particulate matter upon solvation of the polymer is dispersed in the solvent. These dispersed particles significantly decrease the transmission of incident light. For example, suspended carbon black absorbs incident light while suspended titanium dioxide dispersely reflects such light. In either case, the light transmission through the dispersion is significantly reduced. The reduction in transmission is directly related to the initial concentration of the particles in the polymer body. Additionally, if the particles are agglomerated in the polymer, they stay agglomerated in the dispersion and an accurate measure of the effectiveness of the particles as distributed in the polymer is still obtained. Since solvation is a trivial process, the inventive technique is simple and expeditious. These advantages significantly improve quality control measures.

BRIEF DESCRIPTION OF THE DRAWING

The FIGURE is illustrative of results obtained using the inventive process.

DETAILED DESCRIPTION

Since the procedure relies on a relatively stable dispersion of particles, it is generally desirable to utilize the inventive technique with bodies having particles whose median effective diameter is smaller than approximately 100 nm. (Effective diameter is the arithmetic mean diameter as determined from electron micrographs of the particle. If a particle is not spherical then its diameter corresponds to the diameter of the smallest sphere in which it can be inscribed.) Although particles larger than 100 nm are not precluded, the time period which they remain in dispersion is quite short and thus makes measurement inconvenient. Generally, the dispersion should be sufficiently stable so that the level of apparent absorption (see equation 2) measured upon its initial formation is not reduced by more than 20 percent after 24 hours. Although less stable dispersions are measurable with the subject technique, the accuracy of the technique is degraded and is not desirable for products such as compositions employed in outdoor cable jackets where particle concentration critically affects polymer properties.

The particular solvent used to dissolve the polymer is not critical. However, the solvent should be chosen to essentially completely solvate the polymer, i.e., solvate at least 95 percent by weight of the polymer employed without substantially dissolving the particulate material. Additionally, the solvent should not significantly attenuate the light to be employed for the transmission measurement. Typically, the transmission of the sample including solvent, solvated polymer and dispersed solid should be greater than 10 percent of the incident light. For typical samples, the transmission attenuation for the solvent plus the dissolved polymer should generally be less than 20 so that at least 10 percent transmission for the sample is attained. For solvents which produce an acceptable degree of attenuation, the measurement on the actual sample is easily adjusted by the level of attenuation produced by the solvent. For example, a double beam spectrometer is employed with the solvent being placed in the reference beam and the sample with path length equal to that of the solvent being placed in the measurement beam. Most spectrometers automatically compensate the sample signal by an amount commensurate with the reference signal.

The transmission measurement itself is made by standard techniques. (See *Introductory Quantitative Chemistry*, A. R. Olsen et al, W. Y. Freeman and Co., San Francisco, 399–406 (1956) for a description of transmission measurements.) The correlation between the degree of transmission and the concentration of particles in the polymer body is easily determined utilizing a controlled sample. That is, samples are prepared having various particle concentrations and each such sample is measured by the inventive technique. A calibration curve is thus evolved which correlates the initial concentration of particles in the sample with the measured transmission (in terms of apparent absorption as defined in equation 2) of the solvated sample. Determination of concentration is then made by comparing a transmission measurement of a sample with this calibration curve. This is particularly useful where materials such as carbon black are involved which have a degree of absorbence which varies significantly with particle size and degree of dispersion in the polymer. Alternatively, if the particles being measured predominately absorb rather than reflect the measurement light, i.e., the particles are at least 10 times more absorbing than reflecting and the extinction coefficient is known, a simple calculation without calibration is possible. In particular, it is possible to employ the well known relationship, $$A = \ln \frac{I_o}{I} = \ln\left(\frac{1}{T}\right) = \epsilon b c \tag{1}$$

and thus $$A/b = \text{apparent absorption} = \epsilon c \tag{2}$$

where T is the transmittance, $I_o$=incident light intensity, I=light transmitted through the medium, $\epsilon$=extinction coefficient, b=effective path length through the sample, and c=concentration of the absorbing material in weight percent. The effective path length is the path length through the sample times the fraction defined by the total volume of the solution divided into the volume of the dissolved polymer. Thus, calculated concentrations are available for particles which predominantly absorb and whose extinction coefficient is known. The use of a calibration curve is also appropriate for absorbers such as carbon black and for particles such as titanium dioxide which predominantly reflect incident light.

The wavelength of the light employed in the measurement is not critical and is typically in the range 300 nm to 600 nm, preferably 350 nm to 400 nm. To simplify the calculations (when it is appropriate to perform such calculations) this light should have a spectral bandwidth of less than 20 nm. Although broader band light is not precluded, calculations and calibrations become significantly more complicated. Additionally, the wavelength of the light employed should be chosen so that it is not substantially absorbed by the solvent. Additionally, the wavelength should be chosen so that the suspended particles either reflect or absorb but not substantially transmit the light, i.e., less than 10 percent of the light is transmitted by the particles.

It is possible that the polymer body contains more than one particle composition. In this case, the measurement relates to the total particle concentration. However, it sometimes occurs that a combination of particles, although individually suspendable in a solvent, together form an unstable suspension. Thus, for example, with a polymer body having a weight concentration of 1.0 percent by weight carbon black (average particle size 25 nm) and 1.0 percent by weight titanium dioxide (1 $\mu$m average particle size), the titanium dioxide tends to remove a portion of the carbon black from suspension. Thus, in those situations, as previously discussed, a second measurement after a 24 hour delay should be made to ensure that the initial reading has not decreased more than 20 percent. If such decrease has not occurred, then the measured value is related to the total particle concentration by calibration or in the case of appropriate absorbing particles by calculation.

The use of transmission spectroscopy yields an expeditious, reliable and consistent measure of concentration. Since many particles such as carbon black particles primarily absorb, but also to a much lesser extent reflect, the calculations of the concentration from the measured transmission indicates a slightly increased concentration from the actual level. However, the difference between the actual level and the measured level remains substantially constant. Therefore, in bodies having a relatively small concentration of particles, i.e., less than 1.0 percent by weight of the polymer, such measurement errors are sometimes significant and the calibration technique should be used. However, in bodies having a particle concentration greater than 1.0 percent, the errors produced are generally negligible. Thus, if calculation rather than calibration is to be employed, it is preferred that the material have a somewhat higher particle concentration.

In one embodiment, the inventive process is employed for the manufacture of a product. In such an application, a representative portion is taken from material which is to be used or which has been used to produce a product. The portion is tested by the inventive technique and the material or product is either discarded or employed depending on the results of the test.

The following examples are illustrative of the inventive process.

EXAMPLE 1

A Cary Model 219 spectrometer having two matched glass cells measuring 45×12.5×12.5 mm (outside dimensions) were employed. The cells had a 10 mm path length and did not significantly absorb the light employed for the measurement (375 nm wavelength). A 25 ml graduated cylinder was filled with approximately 10 ml of water and the amount of water present was recorded to the nearest tenth of a millimeter. A stirring bar, to be subsequently used in preparing the sample, was then inserted and the new volume measured. The difference between the two readings yielded the volume of the stirring bar. The spectrometer was also calibrated using a dark current adjustment set to zero transmittance and establishing 100 percent transmission by adjusting the slit width for a measurement of pure THF solvent in the reference sample holder.

A 0.0585 g portion of a PVC compound was weighed and was added to a 100 ml volumetric flask. The magnetic stirrer bar was added to the flask together with approximately 75 ml of THF. The solvent was slowly stirred magnetically until the PVC compound was dissolved (approximately 15 to 20 minutes). By examining the flask in a strong light it was easily determined that undissolved PVC was not present. The solvent of the solution was then increased to 98.7 ml (the rest being volume occupied by the stir bar) and the combined solution was vigorously agitated. The solution/dispersion was decanted into a sample cell and its percent transmission, relative to pure THF, was measured within 10 minutes of filling the sample cells. The transmission measured was 22 percent which corresponds to a measured apparent absorption of 332 and a carbon black concentration of 2.3 parts per hundred of resin (phr).

EXAMPLE 2

The accuracy of the procedure described in Example 1 was compared to the ASTM D3349 procedure. Samples of PVC having known quantities of carbon black (0 to 4 parts per hundred by weight of resin) in 0.5 parts per hundred increments were measured by both techniques. The FIGURE shows that both methods gave a straight line dependency of carbon black concentration to apparent absorption coefficient as calculated employing equation 2. As noted earlier, a slightly increased value is obtained by the inventive technique.

What is claimed is:

1. A method for manufacturing a product that comprises a polymer composition that includes particles, said method comprising the steps of obtaining a representative portion of said polymer composition, preparing said representative portion, and performing a spectroscopic measurement on said prepared portion characterized in that said preparation comprises substantially dissolving said portion in a solvent in the substantial absence of the dissolution of said particles to form said prepared portion, measuring the level of light transmitted through said prepared portion, and from said measured level determining the suitability of said polymer composition.

2. The method of claim 1 wherein said particles comprise carbon black.

3. The method of claim 1 wherein said polymer composition comprises polyvinyl chloride.

4. The method of claim 2 wherein said polymer composition comprises polyvinyl chloride.

5. The method of claim 3 wherein said solvent comprises tetrahydrofuran.

6. The method of claim 1 wherein said polymer composition comprises wire jacketing.

7. The method of claim 3 wherein said polymer composition comprises wire jacketing.

8. The method of claim 4 wherein said polymer composition comprises wire jacketing.

9. The method of claim 1 wherein said product comprises an electrical cable.

* * * * *